United States Patent [19]
Kuo et al.

[11] Patent Number: 5,574,168
[45] Date of Patent: Nov. 12, 1996

[54] 1-(SUBSTITUTED BENZYL)-3-(SUBSTITUTED ARYL)-CONDENSED PYRAZOLE DERIVATIVES AND PROCESSES OF MAKING THE SAME

[75] Inventors: Sheng-Chu Kuo; Fang Yu Lee, both of Taichung; Che-Ming Teng, Taipei, all of Taiwan

[73] Assignee: Yung Shin Pharm. Ind. Co., Ltd., Tachia Taichung, Taiwan

[21] Appl. No.: 237,087

[22] Filed: May 3, 1994

[51] Int. Cl.⁶ .................. C07D 231/56; C07D 487/04
[52] U.S. Cl. .................. 548/360.5; 548/361.1; 548/362.5
[58] Field of Search .................. 548/362.5, 360.5, 548/361.1

[56] References Cited

PUBLICATIONS

Yoshina et al. Yakugaku Zasshi (5)1977, 97(9) pp. 955–961.
Yoshina et al. Yakugaku Zasshi (5)1978, 98(2), pp. 204–209.
Streitwieser et al. "Introduction to Organic Chemistry" 3rd Ed(8)1985 by Macmillan Publishing Company (New York) pp. 449–506.

*Primary Examiner*—Johann Richter
*Assistant Examiner*—Laura L. Stockton
*Attorney, Agent, or Firm*—W. Wayne Liauh

[57] ABSTRACT

The invention pertains to a process for preparing (1-substituted benzyl)-3-(hydroxy-carbonyl aryl) condensed pyrazoles or (1-substituted benzyl)-3-(hydroxymethyl aryl) condensed pyrazoles comprising the steps of: (a) reacting compound I and compound II, or compound III and compound IV, to produce compound V, which is a substituted aryl ketone, as follows:

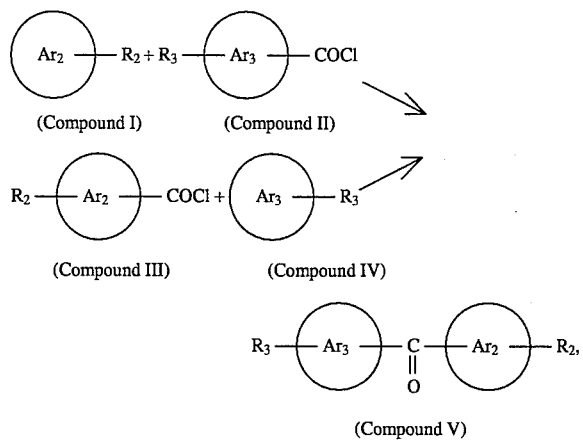

wherein $Ar_2$ and $At_3$ can be, independently,

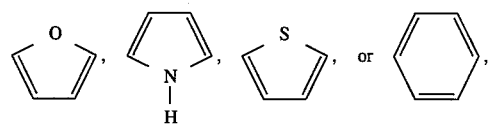

$R_1$ is H, $C_{1-3}$ alkyl, or X (halogen), $R_3$ is H, $C_{1-3}$ alkyl, X (halogen), or —OR radical, and R is H or $C_{1-3}$ alkyl; the process comprising the following steps of: $R_2$ represents $CH_2OR$, H, COOR, $C_{1-3}$ alkyl, or X (halogen); (b) reacting the compound V with a hydrazine compound to form a hydrazone compound; (c) reacting the hydrazone compound compound with trifluoride etherate ($BF_3 \cdot Et_2O$) to form a 1-(substituted benzyl) 3-(substituted aryl) condensed pyraxzole, which is represented by the following formula of

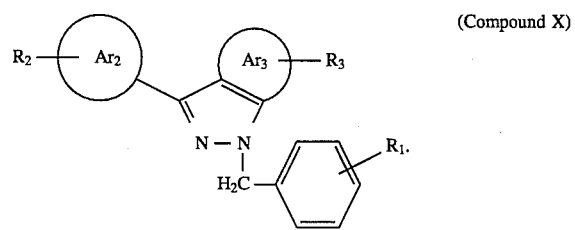

Compound X can be further hydrolyzed or reduced to form corresponding carboxylic acids or alcohols.

5 Claims, No Drawings

1-(SUBSTITUTED BENZYL)-3-(SUBSTITUTED ARYL)-CONDENSED PYRAZOLE DERIVATIVES AND PROCESSES OF MAKING THE SAME

TECHNICAL FIELD OF THE INVENTION

The present invention relates to new and useful condensed pyrazole derivatives, especially to 1-(substituted benzyl)-3-substituted daryl)condensed pyrazole derivatives.

BACKGROUND OF THE INVENTION

Cardiovascular diseases, especially various forms of thrombosis, such as coronary, embolic, venous and traumatic thrombosis, account for a large number of death per year. In fact it is estimated by the American Heart Association that 54% of all deaths is the United States can be attributed to cardiovascular disease. It is therefore important for us to be familiar with physical, Chemical and Clinical aspects of drugs used to treat these form of thrombosis. Since it is believed that initiation of thrombus formation is dependent on platelet aggregation, the inhibitors of platelet aggregation could be prototypes for drugs that could more effectively combat thrombosis.

A number of inhibitors of platelet aggregation have been usually used clinically in the treatment and prevention of vascular thrombosis. These inhibitors might be divided in to several groups based on their mode of action, wherein aspirin, dipyridamole, ticlopidine, and eicosa pentonoic acid(EPA) are used more frequently. However, because of the untold side effects of these inhibitors, it has prompted us to search for novel compounds possessing more potent inhibiting activity on platelet aggregation.

DETAILED DESCRIPTION

The present invention describes a series of 1-(substituted benzyl)-3-(substituted aryl)condensed pyrazoles which have the formula (A). Showing the general structures of condensed pyrazoles IX, X, and XI;

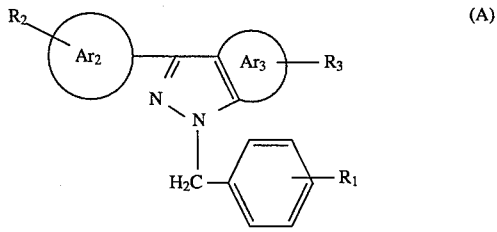

(A)

wherein $R_1$ represents H, $C_{1-3}$ alkyl, X (halogen), —OR, wherein R represents H. $C_{1-3}$ alkyl;

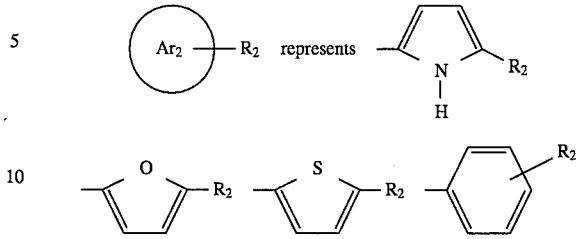

wherein $R_2$ represents —COOR,. —CH$_2$OR, H, $C_{1-3}$ alkyl,

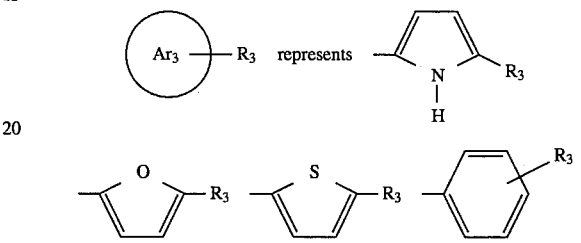

wherein $R_3$ represents H, $C_{1-3}$ alkyl, X (halogen), —OR; wherein R represents H, $C_{1-3}$ alkyl.

The preparation metes compounds(A) are shown in FIG. 1. The methods might be performed using substituted arylcarboxylic acid chloride(II, III) as starting materials, which were treated with substituted aromatic compounds(I,IV) via Friedel-Craft's reaction to form various ketones(V), and then condensed with several hydrazines (VI) to give the corresponding hydrazones(VII). The hydrazones(VII) were further treated with lead tertraacetate(LTA) and boron trifluoride-etherate(BF$_3$.Et$_2$O) according to Yushina,S et al. (Yakugaku Zasshi 97, 955,1977), to give the 1-(substituted benzyl)-3-(substituted aryl)condensed pyrazoles(IX). Hydrolysis of bile ester groups of compounds IX with acids or bases gave the corresponding carboxylic acid derivatives(X). The ester grottos of compounds IX might be reduced with strolls -educible agents eg. LiAlH$_4$ or CaBH$_4$ to hydroxymethyl group and it thus gave alcohols(XI). These structures of compounds of formula A described above were assigned according to the IR, NMR, MS, elemental analytical data.

FIG. 1

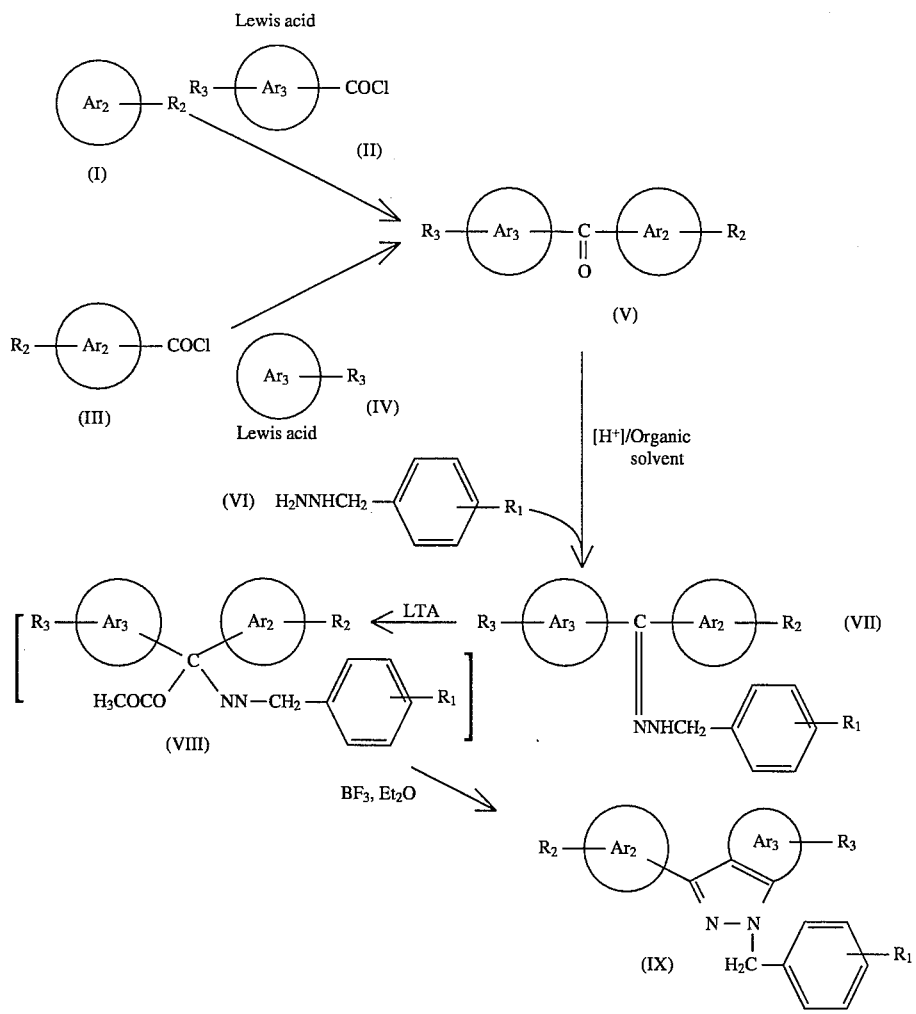

The pharmacological activity of these compounds were determined according to Born,G.C.R. by turbidimetry (J. Physiol. 168, 178, 1963). Based on the method samples were suspended in rabbit platelets which were washed with platelet-rich plasma, the aggregation was then counted by the Lumi-aggregometer(Model 1020, Paytoon, Canada). The results are shown in Tab. 1. Compounds of formula(A) at the concentration of 100 μg/ml are found to inhibition the platelet aggregation perfectly which was induced by arachidonic acid(AA, ADP, collagen and PAF. Since the structures of these compounds are different from these of known antiplatelet agents, the present invention have the potential for farther development.

The pharmaceutical preparations according to the invention which contains confounds of the formula I or pharaceutically acceptable salts thereof are those for enteral or parenternal administration which contain the pharmaceutically active ingredient by itself or together with a pharmaceutically acceptable carrier material. Suitable carriers for oral dosage form are, in particular, fliers, such as sugars, for example lactose, sucrose, mannitol, and furthermore binders, such as starch mucilage using, for example, wheat, rice or potato starch, and/or, if desired, distegrating or adjuncts. Those carriers for parenteral dosage from are, in particular, aqueous solutions and furthermore lipophilic solvents or vehicles, such as fatty oils, and/or, if desired, viscosity-increasing substance, for example, sodium carboxymethyl-cellulose, sorbitol.

The synthetical methods and the experiments of pharmacological evaluation of these compounds are describe as follows.

(I) Synthesis (I-1) Preparation of the Substituted Aryl-Substitute Daryl ketones V

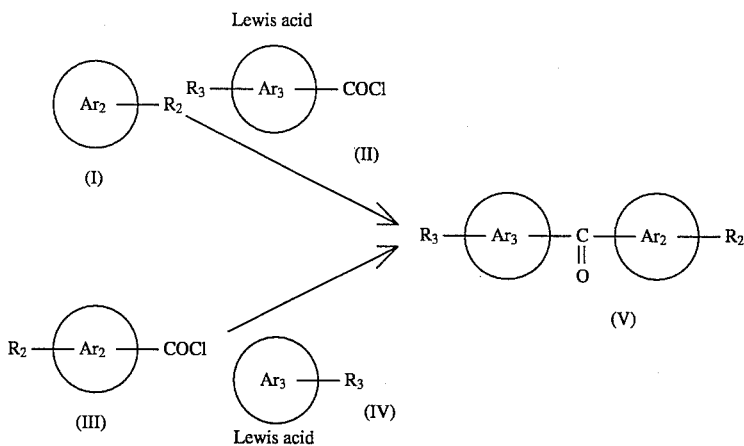

$R_2$ represents —COOR, H, X(halogen), wherein R represents $C_{1-3}$ alkyl. The $R_3$ $Ar_2$ $Ar_3$ were defined in formula (A).

The preparation of the intermediates V via Friedel-Craft's reaction is shown in scheme 1. Where substituted arylcarboxylic acid chloride(II,III) mere used as starting materials to acylate the substituted aromatic compounds I,IV in organic solvents in the presence of Lewis acid to form the corresponding ketones V, and these structures were determined according to the IR, NMR, MS, elemental analytical data.

EXAMPLE I-1-1

5-Methoxycarbonyl-2-furyl phenyl ketone (V-1)

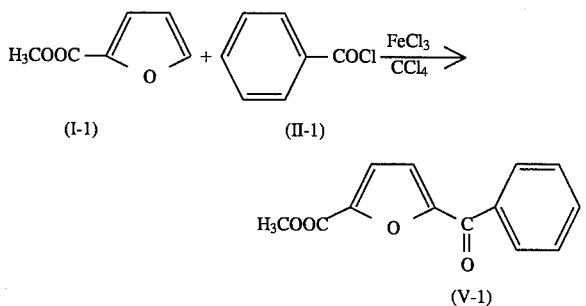

Compound V-1 was reported by Yushina,S. et al.(Yakugaku Zasshi 97,955, 1977). The synthesis is described as follows.

Anhydrous ferric chloride 10.42 g, 0.0026 mole) and benzoyl chloride II-1(29.65 g, were dissolved in $CCl_4$ (40 ml and added dropwise with methyl furan-2-carboxylate I-1 (24 g. 0.19 mole). The reaction mixture was then heated under refluxing for 16 hrs, and after cooling was added with water(120 ml). The mixture was extracted with $CCl_4$, then the $CCl_4$ layer was washed with water, 5% sodium bicarbonate solution, and then with water, till neutral, then dried over anhydrous Magnesium sulfate and filtered. The solvent of the filtrate was evaporated under reduced pressure, the residue was recrystallized from isopropanol, and then from methanol to give compound V-1. Yield 18.75 g(42.9%).
mp: 70°~73° C.
MS(%),m/z: 230 (100) (M⁺).
IR(KBr) $\upsilon_{max}$: 1720, 1650 cm⁻¹ (C=O).
¹H-NMR (CDCl₃) δ:

3.86 (3H, S, CH₃),
7.26–7.32 (2H, m, $C_{3',5'}$-H),
7.40–7.65 (3H, m, $C_{3,4,4'}$-H),
8.05–8.10 (2H, m, $C_{2',6'}$-H).
Anal. Calcd for $C_{13}H_{10}O_4$: C, 67.82; H. 4.38.
Found : C, 67.60; H. 4.21.

EXAMPLE I-1-2

5-(Methoxycarbonyl-2-furyl 4-methylphenyl ketone (V-2)

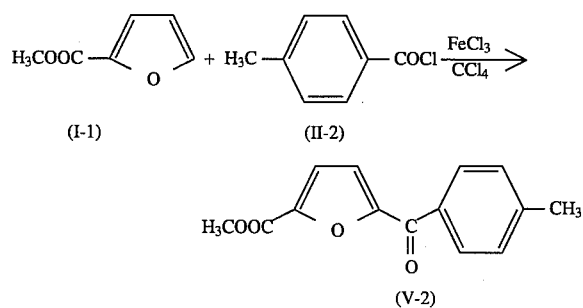

4-Methylbenzoyl chloride(II-2) (31 g, 0.20 mole) as used as the starting material, and treated according to the procedure described in example I-1-1 to give compound V-2.
Yield, 17.0 g(36.7%)
mp: 102°~104° C.
MS(%),m/z: 244 (100) (M⁺)
IR(KBr) $\upsilon_{max}$: 1730, 1650 cm⁻¹ (C=O).
¹H-NMR (CDCl₃) δ:

2.45 (3H, S, CH₃),
3.95 (3H, S, OCH₃),
7.26–7.35 (4H, m, $C_{3,4,3',5'}$-H),
8.00(2H, d, J=8.0 Hz, $C_{2',6'}$-H)
Anal. Calcd for $C_{14}H_{12}O_4$: C, 68.85; H. 4.95.
Found: C, 68.61; H. 4.75.

EXAMPLE I-1-3

5-Methoxycarbonyl-2-furyl 4'-methoxyphenyl ketone (V-3)

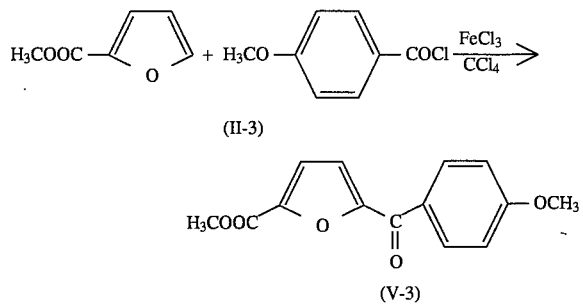

(V-3)

4-Methoxybenzoyl chloride(II-3) (35.7 g, 0.21 mole) was used as the starting material, and treated according to the procedure described in example I-1-1 to give compound V-3. Yield, 21.7 g (43.9%).
mp: 99°~102° C.
MS(%),m/z: 260 (100) (M$^+$).
IR(KBr) $\upsilon_{max}$: 1730, 1650 cm$^{-1}$ (C=O).
$^1$H-NMR (CDCl$_3$) δ:
  3.90 (3H, S, —OCH$_3$),
  3.96 (3H, S, —COOCH$_3$),
  7.00 (2H, d, J=7.8 Hz, C$_{3',5'}$-H),
  7.26–7.32 (2H, m, C$_{3,4}$-H),
  8.15 (2H, d, J=7.8 Hz, C$_{2',6'}$-H).
Anal. Calcd for C$_{13}$H$_9$FO$_4$: C, 64.61; H, 4.65.
  Found: C, 64.39; H. 4.90.

EXAMPLE I-1-4

4-Fluorphenyl 5-methoxycarbonyl-2-furyl ketone(V-4)

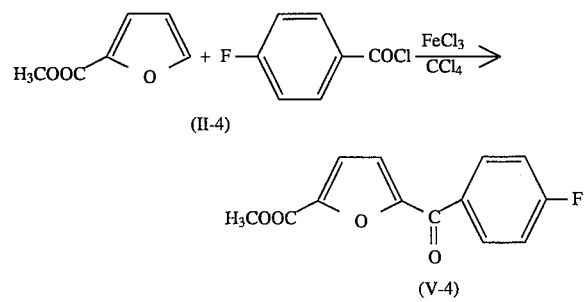

(V-4)

4-Fluorobenzoyl chloride(II-4) (33 g, 0.21 mole) was used as the starting material, and treated according to the procedure described in example I-1-1 to give compound V-4. Yield, 27.4 g(58.1%).
mp: 102°~105° C.
MS(%),m/z: 236 (100) (M$^+$).
IR(KBr) $\upsilon$Max: 1740, 1660 cm$^{-1}$ (C=O).
$^1$H-NMR (CDCl$_3$) δ:
  3.89 (3H, S, CH$_3$),
  7.40–7.53 (4H, m, C$_{3,4,3',5'}$-H,
  8.01–8.09 (2H, m, C$_{2',6'}$-H)
Anal. Calcd for C$_{13}$H$_9$FO$_4$: C, 62.91; H, 3.66.
  Found: C, 61.20; H, 3.90.

EXAMPLE I-1-5

5-Methoxycarbonyl-2-furyl 2'-thiophenyl ketone(V-5)

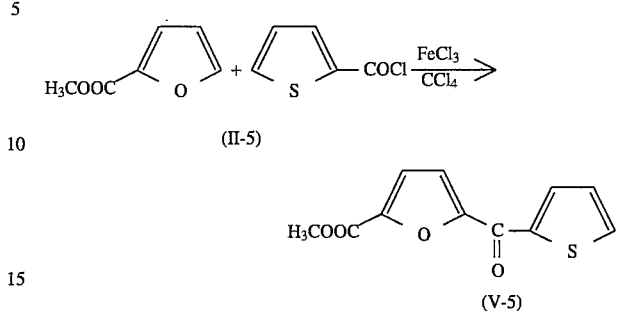

(V-5)

Thiophene-2-carboxylic acid chloride(II-5) (30.5 g, 0.21 mole)was used as the starting material, and treated according to the procedure described in example I-1-1 to give compound V-5. Yield, 28.7 g (63.8%)
mp: 103°~106° C.
MS(%),m/z: 236 (100) (M$^+$).
IR(KBr) $\upsilon_{max}$: 1720, 1620 cm$^{-1}$ (C=O).
$^1$H-NMR (CDCl$_3$) δ:
  3.98 (3H, S, CH$_3$),
  7.22–7.31 (2H, m, C$_{3,4}$-H),
  7.41 (1H, d, J=3.5 Hz, C$_4$-H),
  7.76 (1H, d, J=3.5 Hz, C$_3$-H),
  8.36 (1H, d, J=4.5 Hz, C$_5$-H),
Anal. Calcd for C$_{11}$H$_8$O$_4$S: C, 55.93; H, 3.41.
  Found: C, 55.71; H. 3.23.

EXAMPLE I-1-6

5-Methyl-2-furyl phenyl ketone(V-6)

The compound V-6 was reported by Yushina,S. et al.(Yakugaku Zasshi 97,955, 1977). The synthesis is describes as follow.

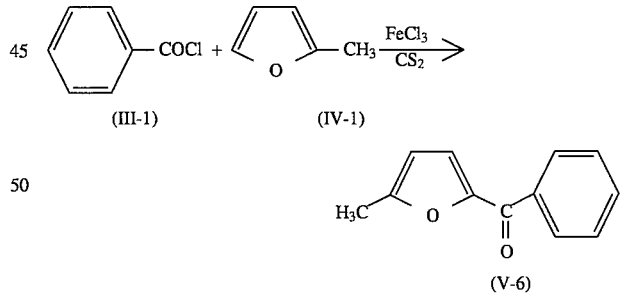

(V-6)

Anhydrous ferric chloride(20 g) and benzoyl chloride(III-1) (10.5 g, 0.075 mole), were dissolved in carbon disulfide(100 ml) and stirred at 20° C. and added dropwise with a solution of 2-methylfuran(IV-1)(12.3 g, 0.15 mole) in 100 ml carbon disulfide(CS$_2$). The reaction mixture under was heated refuxing. After cooling, the mixture was added slowly with 10% HCl(600 ml) solution and then extracted with CCl$_4$, the CCl$_4$ layer was washed with water. 5% sodium bicarbonate(NaHCO$_3$) solution, and then with water till neutral, then dried over anhydrous magnesium sulfate and filtered. The solvent of the filtrate was evaporated and the residue as purified by column chromatography(silica gel-benzene) to give compound V-6, as colorless liquid. Yield, 7.0 g (50%).
MS(%),m/z: 186 (100) (M⁺).
IR(KBr) $\upsilon_{max}$: 1700 cm⁻¹ (C=O).
¹H-NMR (CDCl₃) δ:
  2.37 (3H, S, CH₃),
  6.13 (1H, d, J=3.5 Hz, C₄-H),
  7.03 (1H, d, J=3.5 Hz. C₃-H),
  7.20–7.90 (5H, m, phenyl-H).

EXAMPLE I-1-7

5-Methyl-2-furyl p-methylphenyl ketone (V-7)

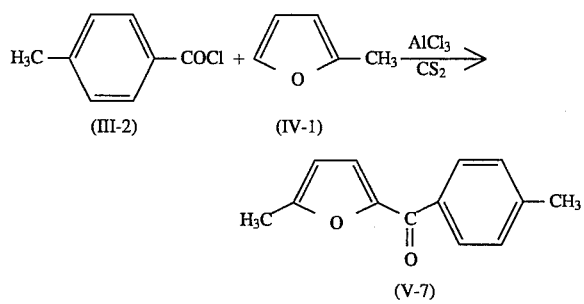

p-Methylbenzoyl chloride(III-2) (11.6 g, 0.075 mole) was used as the starting material and treated according to the procedure described in example I-1-6 to give compound V-7, as colorless liquid. Yield, 7.5 g (50%).
MS(%),m/z: 200 (100) (M⁺).
IR(KBr) $\upsilon_{max}$: 1655 cm⁻¹ (C=O).
¹H-NMR (CDCl₃) δ:
  2.37 (3H, S, C₅-CH₃),
  2.45 (3H, S, C₄'-CH₃),
  6.15 (1H, d, J=3.5 Hz, C₄-H),
  7.02 (1H, d, J=3.5 Hz, C₃-H),
  7.20 (2H, d, J=7.0 Hz, C₃',₅'-H),
  7.90 (2H, d, J=7.0 Hz, C₂',₆'-H),

EXAMPLE I-1-8 p-Chlorophenyl-5-methoxycarbonyl-2-furyl ketone(V-8)

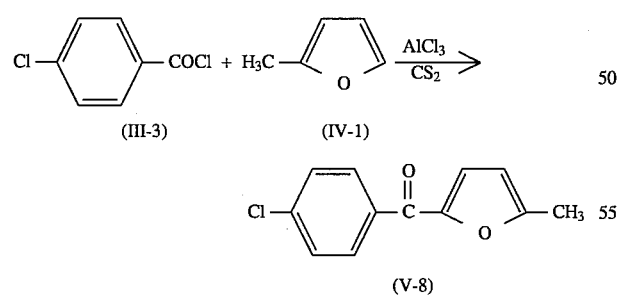

4-Chlorobenzoyl chloride(III-3) (13.1 g, 0.075 mole) was used as the starting material and treated according to the procedure described in example I-1-6 to give compound V-8, as colorless liquid. Yield, 10 g (60%).
MS(%), m/z: 220 (100) (M⁺).
IR(KBr) $\upsilon_{max}$: 1680 cm⁻¹(C=O).
¹H-NMR (CDCl₃) δ:
  2.40 (3H, S, CH₃),
  6.18 (1H, d, J=3.5 Hz, C₄-H),
  7.18 (1H, d, J=3.5 Hz, C₃-H),
  7.35–7.85 (4H, m, phenyl-H).

EXAMPLE I-1-9 p-Chloro-phenyl 5-methyl-2-thienyl ketone(V-9)

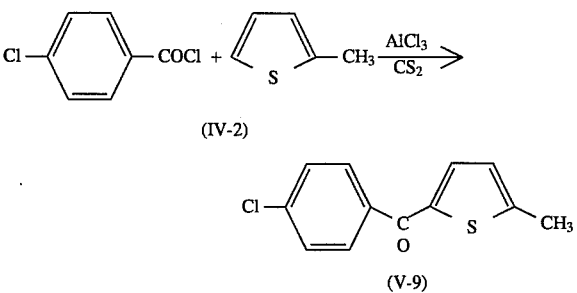

p-Chlorbenzoyl chloride(III-3) (13.1 g, 0.075 mole) was used as the starting material and treated with 2-methyl-thiophene(IV-2)(15 g, 0.15 mole) according to the procedure described in example I-1-6 to give compound V-9, as colorless liquid. Yield, 11.7 g(66%)
MS(%),m/z: 236 (100) (M⁺)
IR(KBr) $\upsilon_{max}$: 1680 cm⁻¹(C=O).
¹H-NMR (CDCl₃) δ:
  2.57 (3H, S, CH₃),
  6.72 (1H, d, J=3.5 Hz, C₄-H),
  7.25–7.75 (5H, m, C₃-H, phenyl-H).

(I-2) Preparation of the 1-substituted benzyl-3-substituted aryl condensed pyrazoles IX

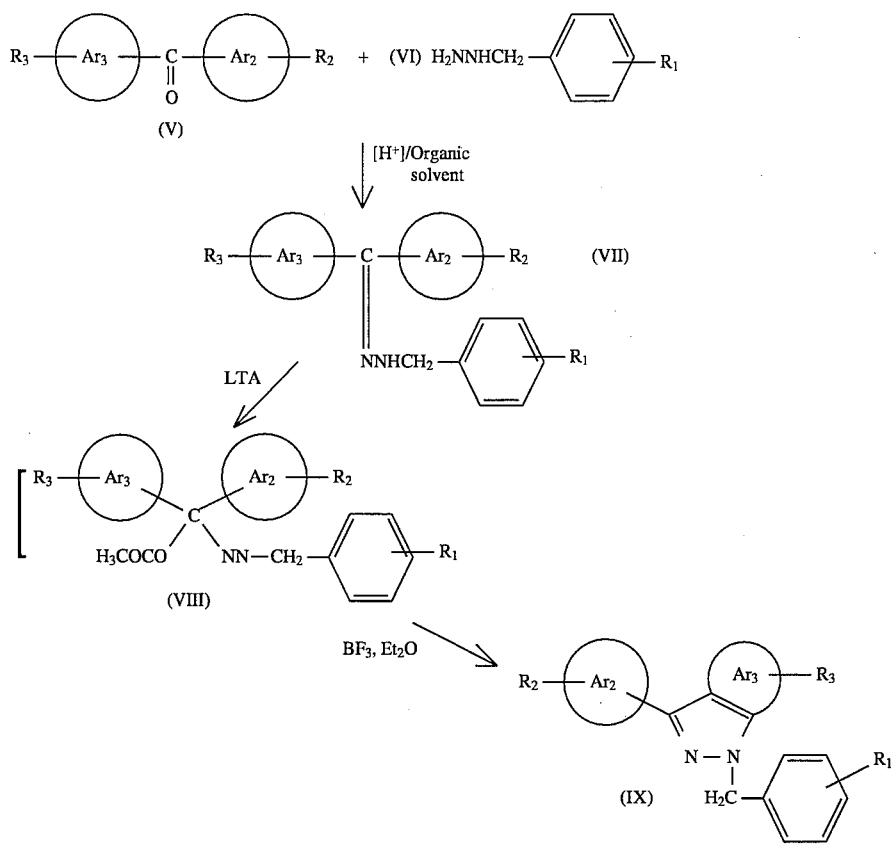

$R_2$ represents —COOR, H, X(halogen), wherein R represents $C_{1-3}$ alkyl. The $R_3$, $Ar_2$, $Ar_3$ were defined in formula (A).

Scheme 2

As shown in scheme 2, the preparation was performed using the intermediate ketones V and substituted benzyl hydrazines(VI) as the starting materials, in organic solvent and Lewis acid under condensed reaction to form the corresponding hydrazones (VII). The residue was purified by column chromatography to give two products, which furthermore converted into each other rapidly to form a mixture. According to Yushina,S. et al., (Yakugaku Zasshi 97, 955, 1977) these two products were the E form and Z form isomer of hydrazones(VII). Since each of the isomer might under go the next reaction to give the same products VIII, no attempt in the present invention was made to separate the E form and Z form isomer but using the hydrazone mixture (VII) in the next reaction. Thus hydrazone mixture (VII) was dissolved in non polar solvent. While stirred vigorously below 40° C., lead tertraacetate(LTA) and boron trifluoride-etherate(BF$_3$·Et$_2$) mixture were added to oxidize and cyclize the compound. The products were purified by column chromatography,recrystallized to give the corresponding 1-substituted benzyl)-3-(substituted aryl)-condensed pyrazoles IX. The structures of these compounds were determined according to the IR, NMR, MS, and elemental analytical data.

EXAMPLE I-2-1

1-Benzyl-3-(5"-methoxycarbonylfurl)-indazole
(IX-1)

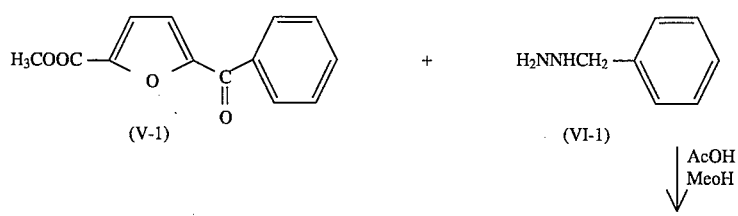

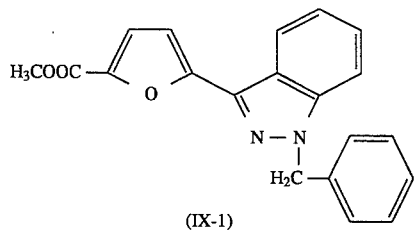
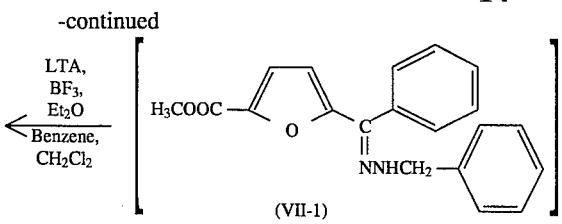

-continued

5-Methoxycarbonyl-2-furylphenyl ketone(V-1) (5.52 g, 0.024 mole) was dissolved in methanol(60 ml), added with benzylhydrazine(VI-1) (9 g, 0.074 mole) and acetic acid (0.5 m) and then heated under refluxing till the reaction was completed. After cooling, the solvent was evaporated and the residue was extracted with chloroform then washed dilute HCl solution, and water till neutral, then dried over anhydrous magnesium sulfate and filtered. The solvent of the filtrate evaporated to give 5"-methoxycarbonylfurylphenyl ketone benzyl hydrazone(VII-1).

The crude product VII-1 was dissolved in 60 ml benzene, then mixed with LTA(28.2 g), BF$_3$·Et$_2$O (12.2 ml), benzene(100 ml), and dichloromethane(100 ml) under stirring. The mixture was poured into ice-water, the organic layer was washed with water, 10% sodium hydroxide solution till neutral, then dried over anhydrous magnesium sulfate and filtered. The solvent of the filtrate was evaporated and the residue was purified by column chromatography (silica gelbenzene) to give compound IX-1. Yield, 0.8 g (10%).
mp: 117°~118° C.
MS(%),m/z: 332 (100) (M$^+$).
IR(KBr) $\upsilon_{max}$: 1720 cm$^{-1}$ (C=O).
$^1$H-NMR (CDCl$_3$) δ:
  3.95 (3H, S, CH$_3$),
  5.66 (2H, S, —CH$_2$—),
  7.02 (1H, J=3.5 Hz, C$_{3''}$-H),
  7.20–7.40 (9H, m, C$_{5,6,7,4''}$,phenyl-H),
  8.26 (1H, d, d, J=8.1, 1.5 Hz, C$_4$-H).

Anal. Calcd for C$_{20}$H$_{16}$N$_2$O$_3$: C, 72.28; H, 4.85; N, 8.43.
Found: C, 72.50; H. 4.60; N. 8.60.

EXAMPLE I-2-2

1-Benzyl-3-(5"-methoxycarbonyl furyl)-6-methylindazole (IX-2)

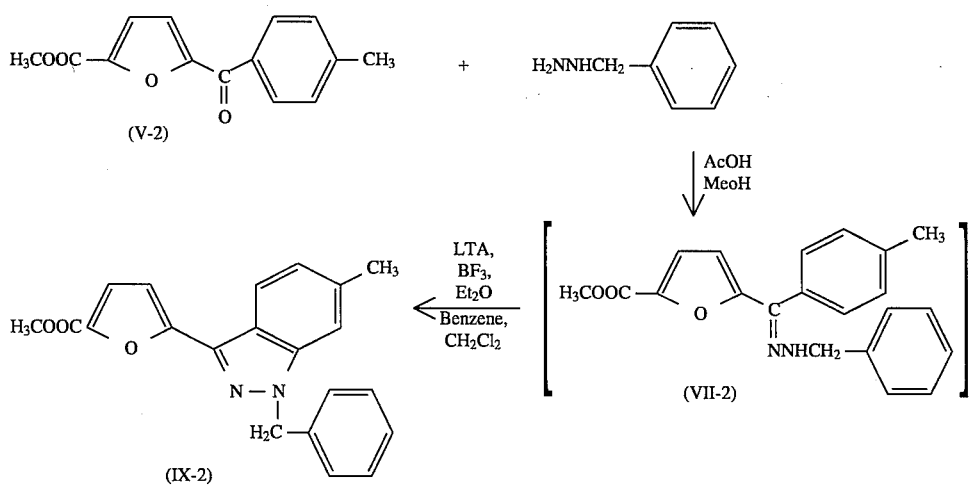

5-Methoxycarbonyl-2-furyl)-4'-methylphenyl ketone (V-2) (5.85 g. 0.024 mole) was used as the starting material and treated, according to the procedure described in example 1-2-1 to give compound IX-2 Yield,1.3 g (16%).

mp: 102°–104° C.
MS(%),m/z: 346 (100) (M+).
IR(KBr) $\upsilon_{max}$: 1720 cm$^{-1}$ (C=O).
$^1$H-NMR(DMSO-d$_6$) δ:
  2.46 (3H, S, —CH$_3$),
  3.87 (3H, S, —OCH$_3$—),
  5.71 (2H, S, —CH$_2$—),
  7.14–7.36 (7H, m, C$_{5,3''}$-H, phenyl-H),
  7.45 (1H, d, J=3.4 Hz, C$_{4'}$-H),
  7.59 (1H, s, C$_7$-H),
  8.10 (1H, d, J=8.0 Hz, C$_4$-H).
Anal. Calcd for C$_{21}$H$_{18}$N$_2$O$_3$: C, 72.82; H, 5.24; N, 8.09.
  Found: C, 72.90; H, 5.21; N, 8.28.

EXAMPLE I-2-3

1-Benzyl-3-(5-methoxycrbonylfuryl)-6-methoxyindazole (IX-3)

3.88 (3H, S, 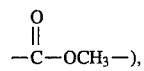), 5.71 (2H, S, —CH$_2$—),
  6.95 (1H, d, J=8.5 Hz, C$_5$-H),
  7.16 (1H, d, J=3.5 Hz, C$_{3''}$-H),
  7.24–7.36 (6H, m, C$_7$-H, phenyl-H),
  7.40 (1H, d, J=3.5 Hz, C$_4$-H),
  7.98 (1H, d, J=8.5 Hz, C$_4$-H).
Anal Calcd for C$_{21}$H$_{18}$N$_2$O$_4$: C, 69.60; H, 5.01; N, 7.73
  Found : C, 69.40; H, 5.21; N, 7.80.

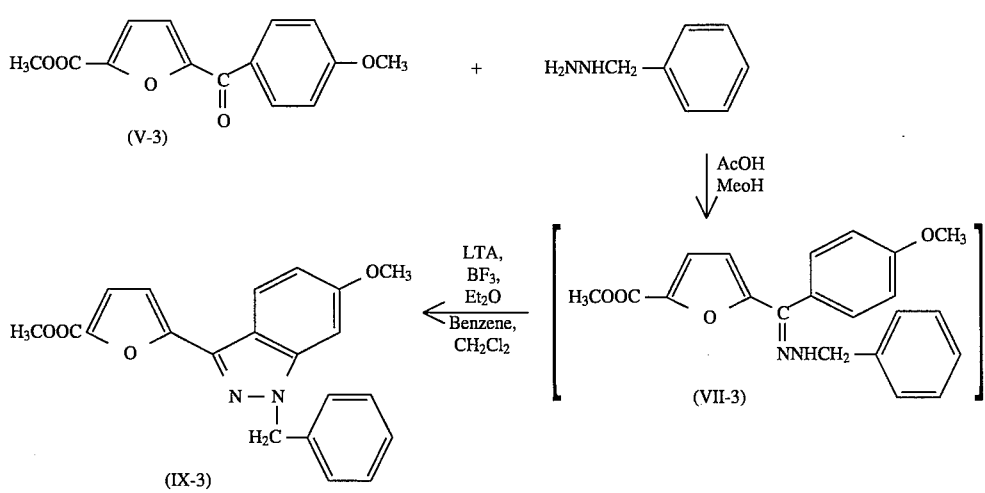

5-Methoxycarbonyl-2-furyl-4'-methylphenyl ketone(V-3) (6.24 g. 0.024 mole) as used as the starting material and treated according to the procedure described in example I-2-1 to give compound IX-3. Yield, 1.8 g (21%).
mp: 108°–109° C.
MS(%),m/z: 362 (100) (M+).
IR(KBr) $\upsilon_{max}$: 1710 cm$^{-1}$ (C=O).
$^1$H-NMR (DMSO-d$_6$) δ:
  3.85 (3H, S, OCH$_3$),

EXAMPLE I-2-4

1-Benzyl-3-(5''-methoxycarbonylfuryl)-6-fluoroindazole (IX-4)

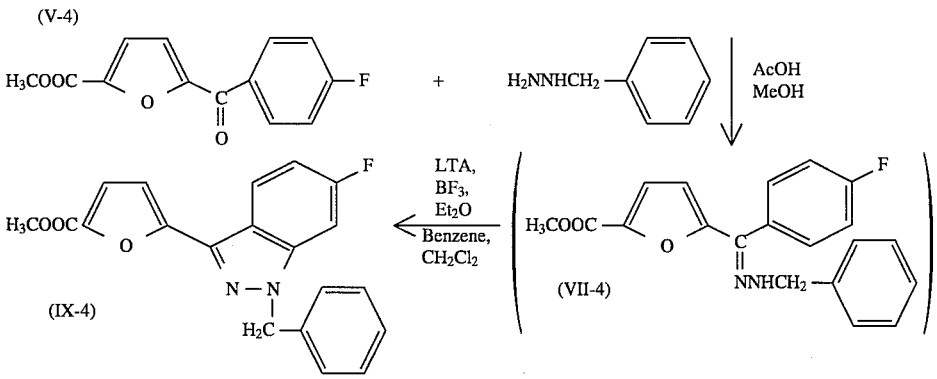

p-Fluorophenyl-5-methoxycarbonyl-2-furyl ketone(V-4) (5.96 g, 0.024 mole) was used as the starting material and treated according to the procedure described in example I-2-1 to give compound IX-4. Yield, 0.4 g (4.8%).
mp: 108°~109° C.
IR(KBr) $\upsilon_{max}$: 1710 cm$^{-1}$ (C=O).
$^1$H-NMR (DMSO-d$_6$) δ:
3.87 (3H, S, CH$_3$),
5.73 (2H, S, —CH$_2$—),
7.18–7.37 (7H, m, C$_{5,3''}$-H, phenyl-H).
7.45 (1H, d, J=3.5 Hz, C$_{4'''}$-H),
7.77 (1H, dd, J=10.0, 1.5 Hz, C$_7$-H),
8.17 (1H, d, d, J=8.0, 6.3 Hz, C$_4$-H).
Anal. Calcd for C$_{20}$H$_{15}$FN$_2$O$_3$: C, 68.57; H, 4.32; N, 8.00.
Found: C, 68.39; H, 4.40; N, 7.90.

EXAMPLE I-2-5

1-Benzyl-3-(5''-methoxycarbonylfuryl)thieno-[3,2-c]pyrazole (IX-5)

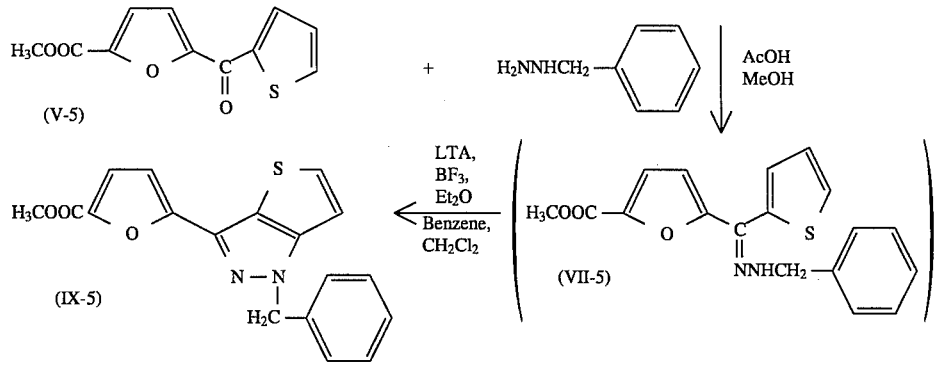

(5-Methoxycarbonyl-2-furyl)-2'-thiophenyl ketone(V-5) (5.7 g, 0.024 mole) was used as the starting material and treated according to the procedure described in example I-2-1 to give compound IX-5. Yield, 1.2 g (14.8%).
mp: 142°~143° C.
MS(%),m/z: 338 (100) (M$^+$).
IR(KBr) $\upsilon_{max}$: 1720 cm$^{-1}$ (C=O).
$^1$H-NMR (DMSO-d$_6$) δ:
3.85 (3H, S, CH$_3$),
5.62 (2H, S, —CH$_2$—),
6.92 (1H, d, J=3.5 Hz, C$_{3''}$-H).

7.24 (1H, d, J=4.8 Hz, C$_6$-H),
7.26–7.35 (5H, m, phenyl-H),
7.43 (1H, d, J=3.5 Hz, C$_{4''}$-H),
7.77 (1H, d, J=4.8, 1.5 Hz, C$_5$-H),
Anal. Calcd for C$_{18}$H$_{14}$N$_2$O$_3$S : C, 63.89; H, 4.17; N, 8.28.
Found: C, 63.71; H, 4.30; N, 8.50.

EXAMPLE I-2-6

1-Benzyl-3-phenyl-5-methylfuro[3,2-c]pyrazole (IX-6)

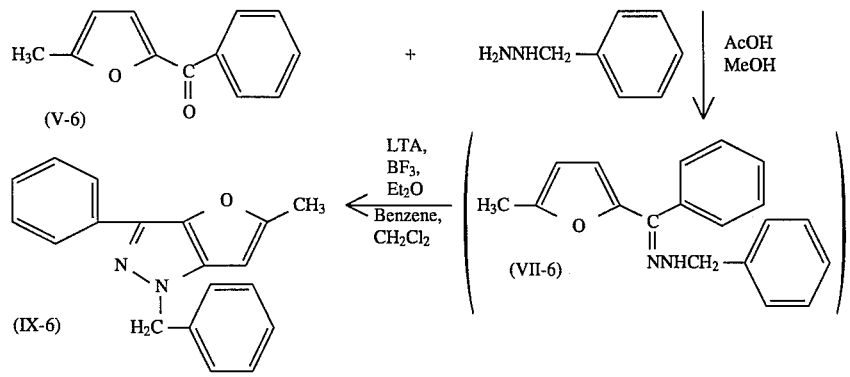

5-Methyl-2-furylphenyl ketone(V-6) (4.5 g, 0.024 mole), was used as the starting material and treated according to the procedure described in example I-2-1 to give compound IX-6. Yield, 2.1 g(30%).
mp: 143°~145° C.
MS(%),m/z: 288 (100) (M$^+$).
$^1$H-NMR (CDCl$_3$) δ:
2.37 (3H, S, CH$_3$), 5.28 (2H, S, —CH$_2$—), 5.53 (1H, S, C$_5$-H), 7.23–8.17 (10H, m, phenyl-H).

Anal. Calcd for CH$_{19}$H$_{16}$N$_2$O: C. 79.14; H, 5.59; N, 9.72.

Found: C, 79.32; H, 5.68; N, 9.52.

EXAMPLE I-2-7

1-Benzyl-3-(p-methylphenyl)-5-methylfuro-[3,2-c]pyrazole (IX-7)

5.50 (1H, S, C$_5$-H)

7.21–8.10 (9H, m, phenyl-H).

Anal. Calcd for C$_{20}$H$_{18}$N$_2$O: C, 79.44; H, 6.00; N, 9.27.

Found: C, 70.21; H, 6.21; N, 9.51.

EXAMPLE I-2-8

1-Benzyl-3-p-chlorophenyl)-5-methyl furo[3.2]pyrazole (IX-8)

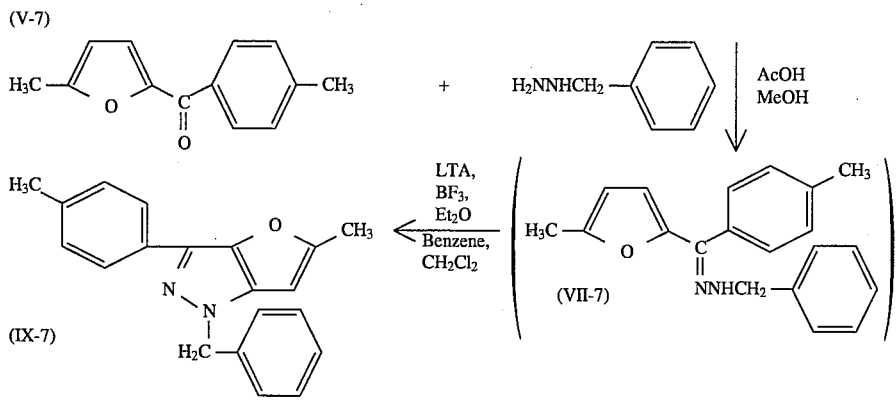

5-Methyl-2-furyl p-methylphenyl ketone(V-7) (4.8 g, 0.024 mole) was used as the starting material and treated according to the procedure described in example I-2-1 to give compound IX-7. Yield, 2.3 g (32%).

mp: 138°~140° C.

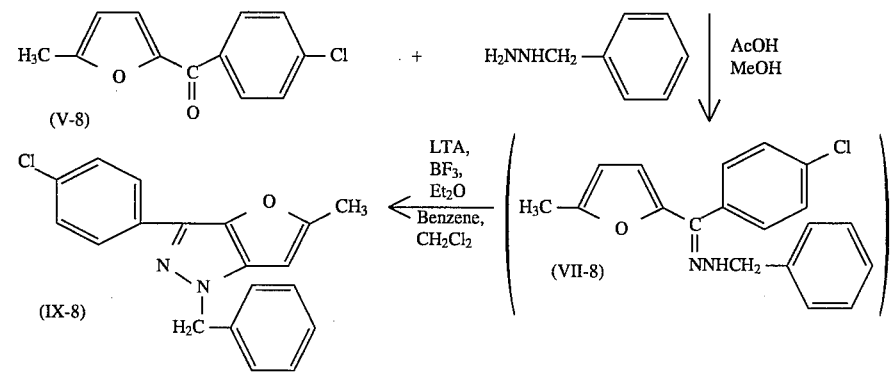

MS(%),m/z: 302 (100) (M$^+$).

$^1$N-NMR (CDCl$_3$) δ:

2.30 (3H, S,

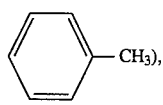

2.36 (3H, S,

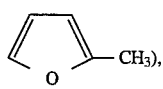

5.28 (2H, S, —CH$_2$—), p-(Chlorophenyl-5-methyl-2 furyl ketone(V-8) (5.3 g, 0.024 mole) was used as the starting material and treated according to the procedure described in example I-2-1 to give compound IX-8. Yield 2.6 g (34%)

mp: 151°~152° C.

MS(%),m/z: 322 (100) (M$^+$).

$^1$H-NMR (CDCl$_3$) δ:

2.34 (3H, S, CH$_3$), 5.34 (2H, S, —CH$_2$—).

6.29 (1H, S, C$_5$-H), 7.43–7.83 (9H, m, phenyl-H).

Anal. Calcd for C$_{19}$H$_{15}$ClN$_2$O: C, 70.70; H, 4.68; N, 8.68.

Found: C, 70.83; H, 4.52; N, 8.78.

EXAMPLE I-2-9

1-Benzyl-3-(p-chlorophenyl)-5-methyl thieno[3,2-c]pyrazole (IX-9)

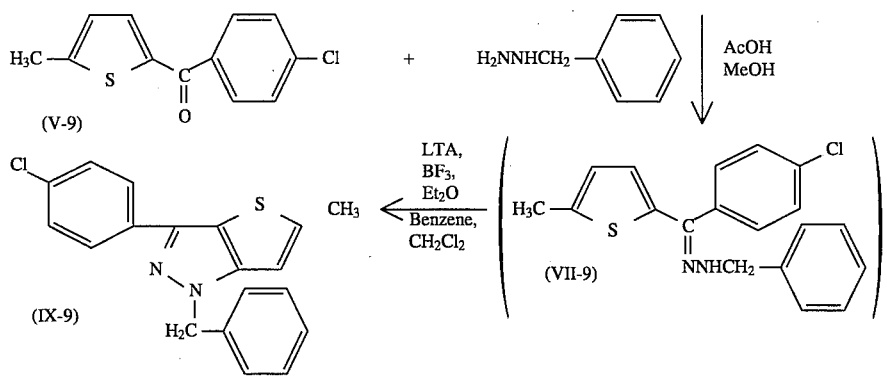

p-Chlorophenyl-5-methyl-2-thienyl ketone(V-9) (5.7 g, 0.024 mole) was used as the starting materials and treated according to the procedure described in example I-2-1 to give compound IX-9. Yield, 2.5 g(30%).
mp: 115°~117° C.
MS(%),m/z: 338 (100) (M+).
$^1$H-NMR (CDCl$_3$) δ:
  2.47 (3H, S, CH$_3$),
  5.43 (2H, S, —CH$_2$—),
  6.35 (1H, S, C$_5$-H),
  7.24–7.79 (9H, m, phenyl-H).
Anal. Calcd for C$_{19}$H$_{15}$ClN$_2$S: C, 67.35; H, 4.46; N, 8.27.
Found: C, 67.53; H, 4.21; N, 8.20.

EXAMPLE I-2-10

1-(p-Methylbenzyl)-3-phenyl-5-methyl furo[3,2-c]pyrazole (IX-10)

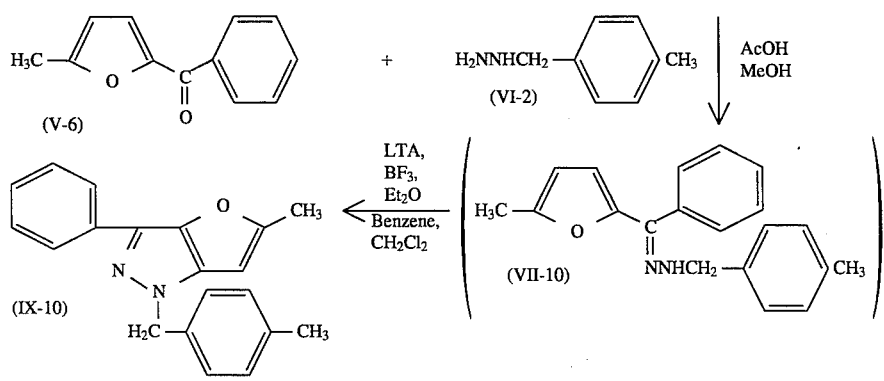

5-Methyl-2-furyl phenylketone(V-6) (4.5 g, 0.024 mole) and p-methylbenzyl hydrazine(VI-2) (10 g, 0.074 mole) were as the starting materials and treated according to the procedure described in example I-2-1 to give compound IX-10. Yield, 2.5 g (35%).
mp: 130°~132° C. MS(%),m/z: 302 (100) (M+).
$^1$H-NMR (CDCl$_3$) δ:

2.31 (3H, S,

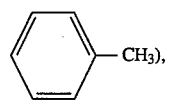

), 2.35 (3H, S,

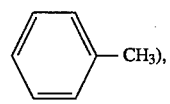

), 5.26 (2H, S, —CH$_2$—),
5.52 (1H, S, C$_5$-H),
7.20–8.00 (9H, m, phenyl-H),
Anal. Calcd for C20H$_{18}$N$_2$O: C, 79.44; H, 6.00; N, 9.26.
Found: C, 79.62; H, 6.30; N, 9.50.

EXAMPLE I-2-11

1-(p-Chlorobenzyl)-3-phenyl-5-methyl-3-furo-[3,2-c]pyrazole (IX-11)

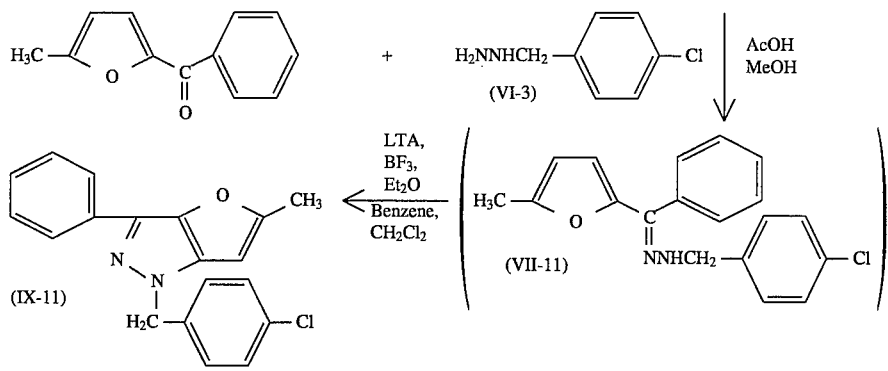

5-Methyl-2-furylphenyl ketone(V-6) (4.5 g. 0.024 moles and p-chloro-benzyl hydrazine(VI-3) (11.4 g, 0.073 mole) were used as the the starting material and treated according to the procedure described in example I-2-1 to give compound IX-11. Yield, 2.3 g (30%).
MS(%),m/z: 322 (100) (M$^+$).
$^1$H-NMR (CDCl$_3$) δ:
2.36 (3H, S, CH$_3$),
5.26 (2H, S, —CH$_2$—),
5.53 (1H, S, C$_5$-H),
7.10–8.10 (9H, m, phenyl-H).
Anal. Calcd for C$_{19}$H$_{15}$ClN$_2$O: C, 70.70; H, 4.68; N, 8.68.
Found: C, 70.90; H, 1.78; N, 8.51.

EXAMPLE I-2-12

1-(p-Methoxybenzyl)-3-phenyl-5-methyl furo[3,2-c]pyrazole (IX-12)

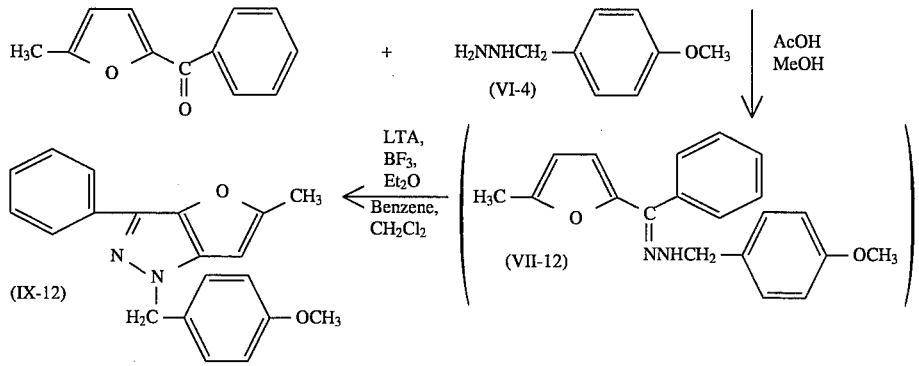

p-Methoxybenzyl hydrazine(VI-4) (11.1 g, 0.073 mole) and 5-methyl-2-furylphenyl ketone(V-6) (4.5 g, 0.024 mole) was used as the starting material and treated according to the procedure described in example I-2-1 to give compound IX-12. Yield, 2.2 g (29%).
mp: 130°–132° C.
MS(%),m/z: 318 (100) (M$^+$).
$^1$H-NMR (CDCl$_3$) δ:
2.35 (3H, S, C$_4$H$_3$),
5.26 (2H, S, —CH$_2$—),
5.55 (1H, S, C$_5$-H),
6.80 (2H, d, J=8.8 Hz, C$_{3',5'}$-H),
7.11–8.10 (7H, m, phenyl-H).
Anal. Calcd for C$_{20}$H$_{18}$N$_2$O$_2$: C, 75.45; H, 5.70; N, 8.80.
Found: C, 75.60; H, 5.51; N, 8.92.

EXAMPLE I-2-13

1-Benzyl-3-(p-ethoxycarbonlphenyl)indazole(1X-13)

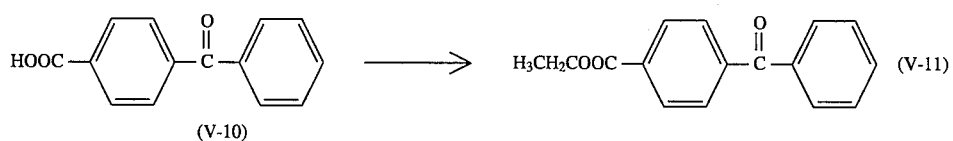

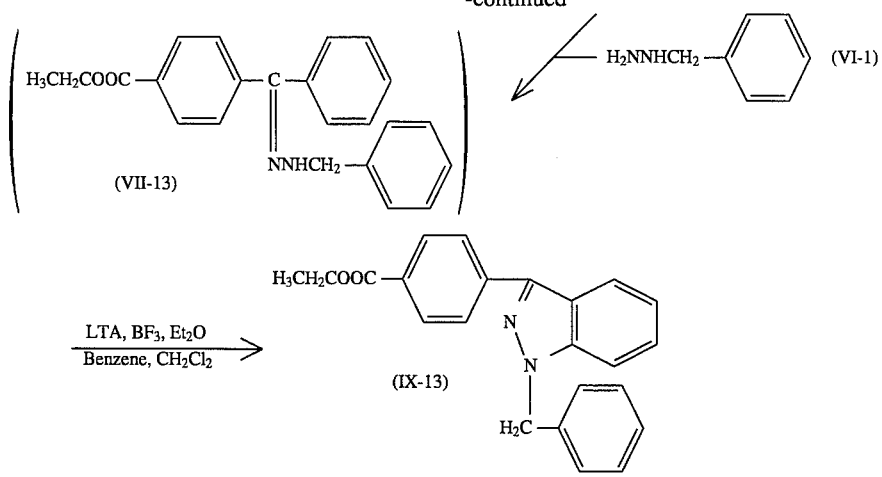

p-Benzoylbenzoic acid (V-10) was reported by Werthein, E. (J.Am. Chem.Soc.55, 2540.1033).

Compound V-10(22.6 g, 0.1 mole) was dissolved in toluene(100 mole). To the solution was added p-toluensulfonic acid(3.0 g) and ethanol(15 ml), and was boiled under reflux for 24 hr. The reaction mixture was poured into ice water. The organic layer was washed with 5% NaHCO$_3$ solution and then with water, dried over anhydrous magnesium sulfate and filtered. The solvent of filtrate was evaporated and the residue was purified by chromatography on silica gel. Elution with benzene, yielded ethyl p-benzoylbenzoate(V-11) (23.0 g, 90%).

Compound V-11(23.0 g, 0.09 mole) and benzyl hydrazine (VI-1) (36.0 g, 0.3 mole) was used as the starting material and treated according to the procedure described in example I-2-1 to give compound 1X-13. Yield. 9.6 g.(30%)
mp: 95°~96° C.
IR(KBr) $\upsilon_{max}$: 1700 cm$^{-1}$ (C=O)
MS(%), m/z: 356 (100) (M$^+$)
$^1$H-NMR (CDCl$_3$) δ:

1.35(3H, t, J=8.0 Hz, —CH$_2$—CH$_3$),
4.35(2H, q, J=8.0 HZ, —CH$_2$—CH$_3$),
5.78(2H, S,

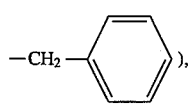), 7.40~8.40(13H, m, aromatic protons)
Anal. Calcd for C$_{23}$H$_{20}$N$_2$O$_2$: C, 77.51, H, 5.66, N, 7.86.
Found: C, 77.30, H, 5.71, N, 7.68

(I-3) Preparation of the 1-substituted benzyl)-3-(hydroxycarbonyl aryl)condensed pyrazoles) (X) and (1-substituted benzyl-3-(hydroxymethylaryl)-condensed pyrazoles (X1)

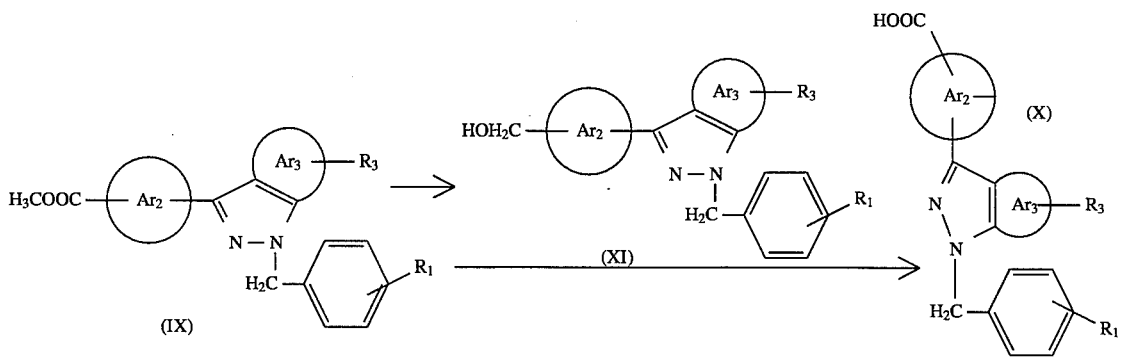

The R$_1$, R$_3$, X, R, Ar$_2$, Ar$_3$ were defined in formula (A)

Scheme 3

As shown in scheme 3, the preparation was performed by hydrolyzing the ester groups of condensed pyrazoles IX with acids or bases to form the corresponding crboxylic acids(X). The ester groups of condensed pyrazoles IX were reduced with some strong reducing agents, ea. LiAlH$_4$ or CaBH$_4$ to the corresponding hydroxymethyl groups to form alcohols(XI).

EXAMPLE I-3-1

1-Benzyl-3-(5"-hydroxycarbonylfurl)-indazole (X-1)

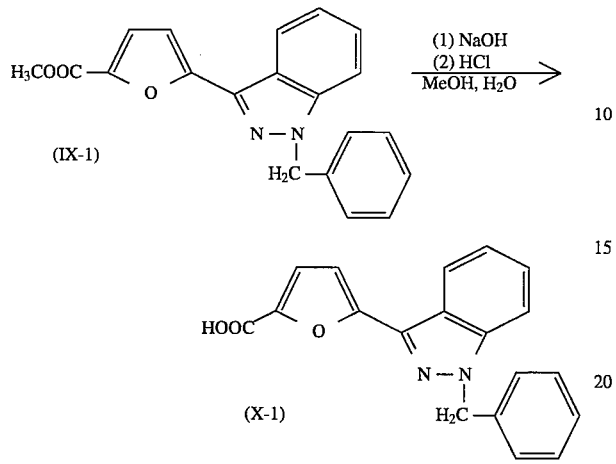

1-Benzyl-3-(5"-methoxycarbonylfurl)-indazole (IX-1) (100 mg, 0.032 mole), was dissolved in a mixture of methanol(8 ml) and sodium hydroxide(7.5 mg) solutions then heated under refluxing. After cooling the solvent was evaporated. The residue was dissolved in water(1.5 ml), then acidified with diluted HCl solution. The crystals were collected, then recrystallized from acetone to give compound X-1. Yield, 73 mg (76.5%).

mp: 202°~203° C.

MS(%),m/z: 318 (100) (M+).

IR(KBr) $\upsilon_{max}$: 3450 cm$^{-1}$(—OH), 1700 cm$^{-1}$ (C=O).

$^1$H-NMR (DMSO-d$_6$) δ:

5.76 (2H, S, —CH$_2$), 7.20 (1H, d, J=3.5 Hz, C$_{3''}$-H), 7.26–7.35 (6H, m, C$_5$-H, phenyl-H), 7.38 (1H, d, J=3.5 Hz, C$_{4''}$-H), 7.49 (1H, t, J=8.2 Hz, C$_6$-H), 7.80 (1H, d, J=8.2, 1.5 Hz, C$_7$-H), 8.15 (1H, d, J=8.1, 1.5 Hz, C$_4$-H).

Anal. Calcd for C$_{19}$H$_{14}$N$_2$O$_3$: C, 71.69; H, 4.43; N, 8.80.

Found: C, 71.91; H, 4.62; N, 8.62.

EXAMPLE I-3-2

1-Benzyl-3-(5"-hydroxycarbonylfurl)-6-methylindazole(X-2)

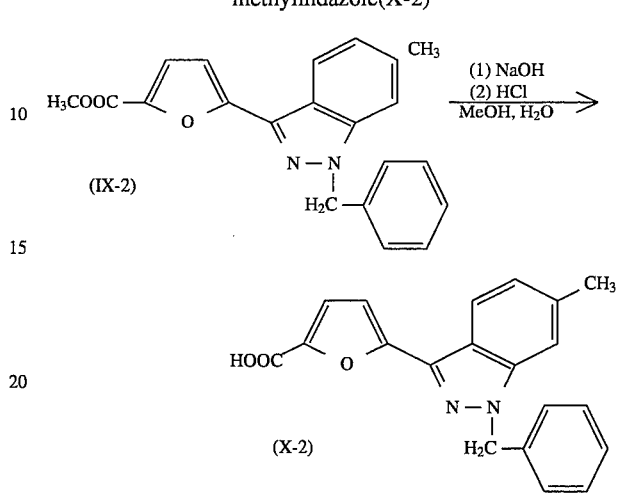

1-Benzyl-3-(5"-methoxycarbonylfuryl)-6-methylindazole (IX-2) (111 mg, 0.032 mole) was used as the starting material, and reated according to the procedure described in example I-3-1 to give compound X-2. Yield, 95 mg (89%).

mp: 201°~202° C.

MS(%),m/z: 332 (100) (M+).

IR(KBr) $\upsilon_{max}$:: 3450 cm$^{-1}$(—OH, 1700 cm$^{-1}$(C=O).

$^1$H-NMR (DMSO-d$_6$) δ:

2.46 (3H, S, —CH$_3$), 5.70 (2H, S, —CH$_2$—), 7.16 (1H, d, J=3.5 Hz, C$_{3''}$-H), 7.23–7.33 (CH, m, C$_5$-H, phenyl-H), 7.38 (1H, d, J=3.5 Hz, C$_{4''}$-H), 7.61 (1H, d, J=1.4 Hz, C$_7$-H), 8.00 (1H, d, J=8.2 Hz, C4-H).

Anal. Calcd for C$_{20}$H$_{16}$N$_2$O$_3$: C, 72.28; H, 4.85; N, 8.43.

Found: C, 72.51; H, 4.96; N, 8.23.

EXAMPLE I-3-3

1-Benzyl-3-(5"-hydroxycarbonylfurl)-6-methoxyindazole (X-3)

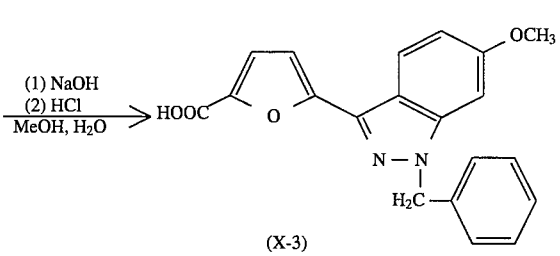

1-Benzyl-3-(5"-methoxycarbonylfuryl)-6-methoxyindazole (IX-3) (116 mg, 0.032 mole) was used as the starting material, and treated according to the procedure described in example I-3-1 to give product X-3. Yield, 86.1 mg (77.3%).
mp: 222°~223° C.
MS(%),m/z: 348 (100) (M⁺).
IR(KBr) $\upsilon_{max}$: 3450 cm$^{-1}$(—OH), 1710 cm-1(C=O).
$^1$H-NMR (DMSO-d$_6$) δ:
3.84 (3H, S, CH$_3$),
5.70 (2H, S, —CH$_2$—),
6.95 (1H, dd, J=8.3, 1.8 Hz, $C_{3''}$-H),
7.12 (1H, d, J=3.4 Hz, $C_{3''}$-H),
7.25–7.38 (7H, m, $C_{7,4''}$-H, phenyl-H),
7.98 (1H, d, J=8.3 Hz, $C_4$-H);
Anal. Calcd for $C_{20}H_{16}N_2O_4$: C, 68.96; H, 4.63; N, 8.04.
Found: C, 68.71; H, 4.39; N, 8.23.

EXAMPLE I-3-4

1-Benzyl-3-(5'-hydroxycarbonylfurl)-6-fluoroindazole(X-4)

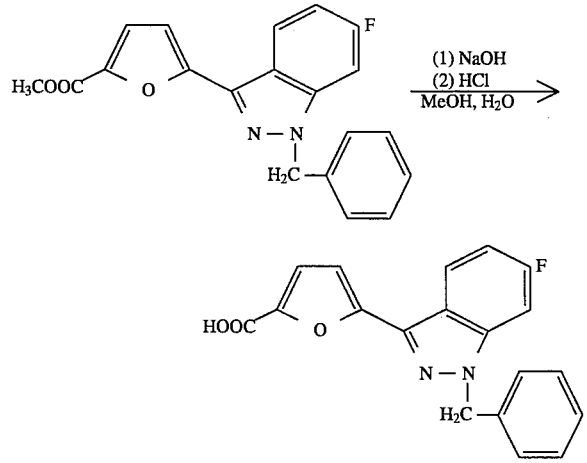

1-Benzyl-3-(5"-methoxycarbonyl furyl)-6-fluoroindazole (IX-4) (112 mg, 0.032 mole) was used as the starting material, andt reated according to the example procedure described in I-3-1 to give compound X-4. Yield, 70 mg (65%).
mp: 252°~253° C.
MS(%),m/z: 336 (100) (M⁺).
IR(KBr) $\upsilon_{max}$: 3450 cm$^{-1}$(—OH), 1690 cm$^{-1}$ (C=O).
$^1$H-NMR (DMSO-d) δ:
5.72 (2H, S, —CH$_2$—),
7.21 (1H, d, J=3.5 Hz, $C_3$-H),
7.23–7.33 (6H, m, $C_5$-H, phenyl-H),
7.39 (1H, d, J=3.5 Hz, $C_4$-H),
7.79 (1H, dd, J=9.8, 1.8 Hz, $C_7$-H),
8.17 (1H, dd, J=8.5, 5.3 Hz, $C_4$-H).
Anal. Calcd for $C_{19}H_{13}FN_2O_3$: C, 67.86; H, 3.90; N, 8.33.
Found: C, 67.97; H, 3.82; N, 8.31.

EXAMPLE I-3-5

1-Benzyl-3-(5"-hydroxycarbonylfurl)-thieno-[3,2-c]pyrazole(X-5)

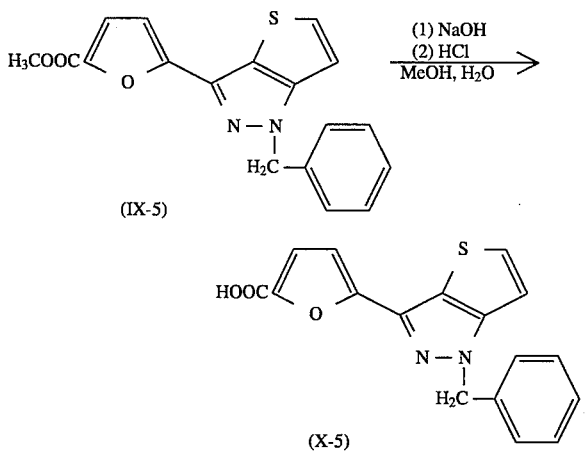

1-Benzyl-3-(5"-methoxycarbonylfuryl)thieno[3,2-c]pyrazole (IX-5) (108 mg, 0.032 mole) was used as the starting material and treated according to the procedure described in example I-3-1 to give compound X-5. Yield. 83.3 mg (80.3%).
mp: 221°~224° C.
MS(%),m/z: 324 (100) (M⁺).
IR(KBr) $\upsilon_{wax}$: 3500 cm$^{-1}$(—OH), 1720 cm$^{-1}$ (C=O).
$^1$H-NMR (DMSO-d$_6$) δ:
5.62 (2H, S, —CH$_2$—),
6.90 (1H, d, J=3.5 Hz, $C_3''$-H),
7.26 (1H, d, J=4.8 Hz. $C_6$-H).
7.25–7.35 (6H, m, $C_4''$-H, phenyl-H),
7.78 (1H, d, J=4.8 Hz. $C_5$-H).
Anal. Calcd for $C_{17}H_{12}N_2O_3$: C, 62.95; H, 3.73; N, 8.64.
Found: C, 62.70; H, 3.51; N, 8.80.

EXAMPLE I-3-6

1-Benzyl-3-(p-hydroxycarbonylphenyl)imdazole(X-6)

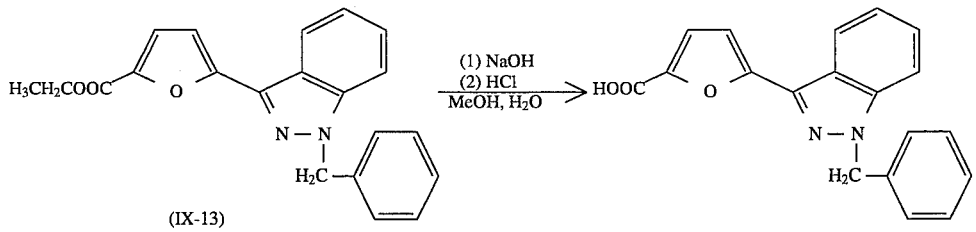

1-Benzyl-3-(p-ethoxycarbonylphenyl)indazole (1X-13) (14 g, 0.04 mole) was used as the starting material and treated according to the procedure described in example I-3-1 to give compound X-6. Yield 9.6 g (75%).
mp: 204°~205° C. (d.)
MS(%), m/z: 328(100)(M$^+$)
IR(KBr) $\upsilon_{max}$: 3500~3300 cm$^{-1}$(OH), 1710 cm$^{-1}$(C=O)
$^1$H-NMR(DMSO-d$_6$) δ:
5.77(2H, S,

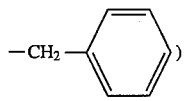)

7.28–8.18(13H, m, aromatic protons)
And. calcd for $C_{21}H_{16}N_2O_2$: C, 76.81; H, 4.91; N, 8.53.
Found: C, 76.98; H, 4.83; N, 8.75.

EXAMPLE I-3-7

1-Benzyl-3-(5"-hydroxymethylfurl)-indazole (XI-1)

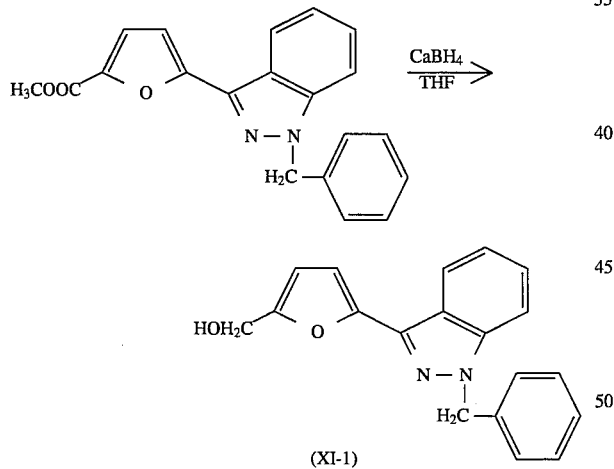

1-Benzyl-3-(5"-methoxycarbonylfurl)-indazole (IX-1) (88 mg, 0.027 mole) was dissolved in a homogenous solution of THF (30 ml) dispersed with calcium borohydride (56 mg, 0.08 m mole). The mixture was heated under refluxing and then filtered. The solvent was evaporated and the residue was recrystallized from n-hexane and the purified by column chromatography (silica gel n-hexane: ethyl acetate) to give compound Xl-1. Yield, 70 mg(87%).
mp: 108°~109° C.
MS(%),m/z: 304 (100) (M$^+$).
IR(KBr) $\upsilon_{wax}$: 3350 cm$^{-1}$ (—OH).
$^1$H-NMR (DMSO-d$_6$) δ:
4.51 (2H, d, J=5.5 Hz, —CH—O—), 5.31 (1H, t, J=5.5 Hz, —OH),
5.70 (2H, S,

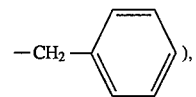), 6.47 (1H, d, J=3.4 Hz, C$_{4''}$-H),
6.95 (1H, d, J=3.4 Hz, C$_{3''}$-H),
7.20–7.35 (6H, m, C$_5$-H, phenyl-H),
7.44 (1H, t, J=8.2 Hz, C$_6$-H),
7.73 (1H, dd, J=8.2, 1.8 Hz, C$_7$-H),
8.11 (1H, dd, J=8.2, 1.0 Hz, C$_4$-H).
Anal. Calcd for $C_{14}H_{16}N_2O_2$: C, 74.98; H, 5.30; N, 9.20.
Found: C, 74.76; H, 5.61; N, 9.31.

EXAMPLE I-3-8

1-Benzyl-3-(5"-hydroxymethylfurl)-6-methylindazole(XI-2)

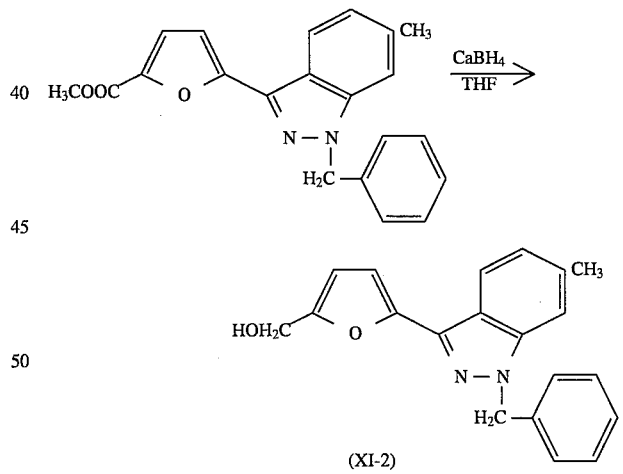

1-Benzyl-3-(5"-methoxycarbonylfuryl)-6-methylindazole (Ides) (92 mg, 0.027 mole) was used as the starting material and treated according to the procedure described in example I-3-7 to give compound XI-2. Yield, 74 mg (88%).
mp: 112°~114° C.
MS(%),m/z: 318 (100) (M$^+$).
IR(KBr) $\upsilon_{max}$: 3400 cm$^{-1}$ (—OH).
$^1$H-NMR (DMSO-d$_6$)
2.44 (3H, S, CH$_3$),
4.50 (2H, d, J=5.2 Hz, —CH$_2$—O—),
5.30 (1H, br, —OH), 5.64 (2H, S,

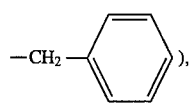
), 6.45 (1H, d, J=3.3 Hz, $C_{4''}$-H),
6.02 (1H, d, J=3.3 Hz, $C_{3''}$-H),
7.08 (1H, dd, J=8.3, 1.0 Hz, $C_5$-H),
7.19–7.36 (5H, m, phenyl-H),
7.52 (1H, d, J=1.0 Hz, $C_7$-H),
7.98 (1H, dd, J=8.3, 1.0 Hz, $C_4$-H).
Anal. Calcd for $C_{20}H_{18}NO_2$: C, 75.45; H, 5.70; N, 8.80.
Found: C, 71.50; H, 5.52; N, 8.09.

EXAMPLE I-3-9

1-Benzyl-3-(5"-hydroxymethylfuryl)-6-methoxylindazole(XI-3)

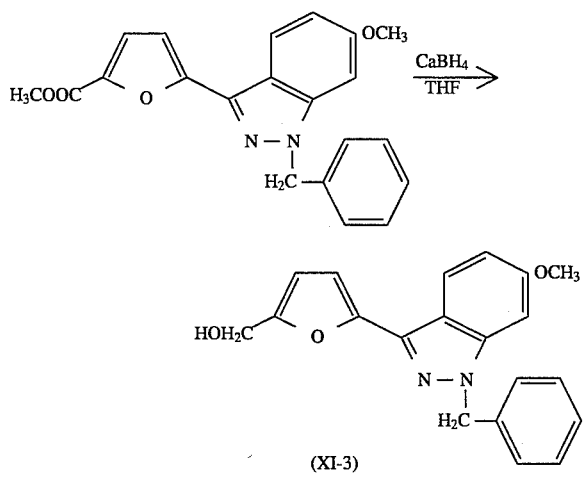

1-Benzyl-3-(5"-methoxycarbonylfuryl)-6-methoxyindazole (IX-3) (96 mg, 0.027 mole) was used as the starting material and treated according to the procedure described in example I-3-7 to give compound XI-3. Yield, 80 mg (90%).
mp: 109°–110° C.
MS(%),m/z: 334 (100) ($M^+$).
IR(KBr) $\upsilon_{max}$: 3300~3400 $cm^{-1}$(—OH).
$^1$H-NMR (CDCl$_3$) δ:
 1.90 (1H, br, OH),
 3.80 (3H, S, —$CH_3$),
 4.74 (2H, d, J=4.9 Hz, —$CH_2$—O—),
 5.59 (2H, S,

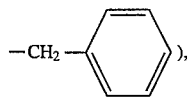
), 6.47 (1H, d, J=3.2 Hz, $C_{4''}$-H),
 6.59 (1H, d, J=2.0 Hz, $C_7$-H),
 6.84 (1H, d, J=3.2, 1.0 Hz, $C_{3''}$-H),
 6.88 (1H, dd, J=8.5, 1.5 Hz, $C_5$-H),
 7.17–7.31 (5H, m, phenyl-H),
 7.91 (1H, d, J=8.5 Hz, $C_4$-H).
Anal. Calcd for $C_{20}H_{18}N_2O_3$: C, 71.84; H, 5.43; N, 8.38.
Found: C, 71.65; H, 5.25; N, 8.51.

EXAMPLE I-3-10

1-Benzyl-3-(5"-hydroxymethylfurl)-6-fluoroindazole (XI-4)

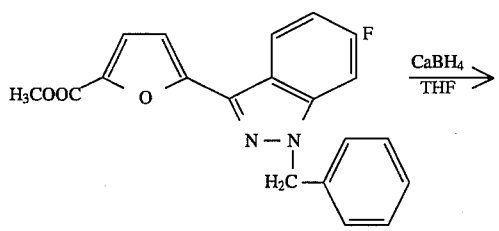

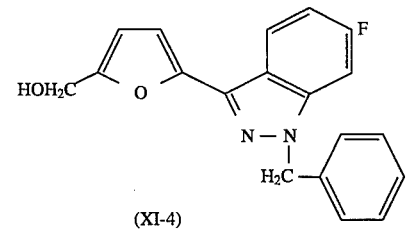

1-Benzyl-3-(5"-methoxycarbonylfuryl)-6-fluoroindazole (IX-4) (93 mg, 0.027 mole) was used as the starting material and treated according to the procedure described in example I-3-7 to give compound XI-4. Yield, 75 mg (88%).
mp: 110°–112° C.
MS(%),m/z; 322 (100) ($M^+$).
IR(KBr) $\upsilon_{max}$: 3450 $cm^{-1}$ (—OH).
$^1$H-NMR (DMSO-d$_6$) δ:
 4.49 (2H, br, —$CH_2$—O—),
 5.45 (1H, br, —OH)
 5.88 (1H, S,

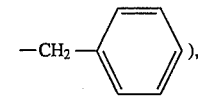
), 6.48 (1H, d, J=3.2 Hz, $C_{4''}$-H),
 6.98 (1H, d, J=3.2 Hz, $C_{3''}$-H),
 7.10–7.18 (1H, m, $C_5$-H),
 7.24–7.36 (5H, m, phenyl-H),
 7.70 (1H, dd, J=10.0, 2.0 Hz, $C_7$-H),
 8.15 (1H, dd, J=8.5, 5.1 Hz, $C_4$-H).
Anal. Calcd for $C_{19}H_{15}FN_2O_2$: C, 70.80; H, 4.60; N, 8.69.
Found: C, 70.59; H, 4.41; N, 8.41.

EXAMPLE I-3-11

1-Benzyl-3-(5"-hydroxymethylfurl)-thieno-[3,2-c]pyrazole(XI-5)

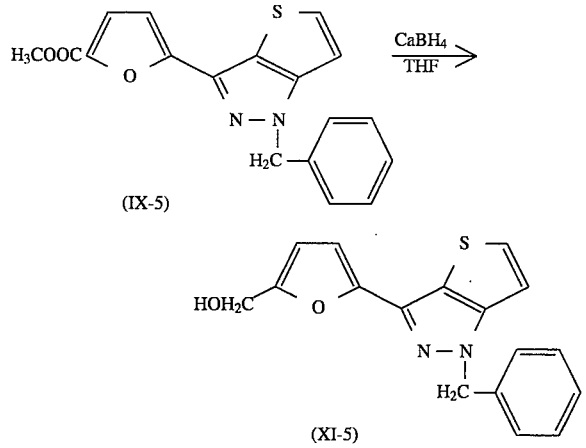

1-Benzyl-3-(5"-methoxycarbonylfuryl)thieno[3,2-c]pyrazole (IX-5) (90 mg, 0.027 mole) was used as the starting material and treated according to the procedure described in example I-3-6 to give compound XI-5, Yield, 63.4 mg (76%).
mp: 103°~104° C.
MS(%),m/z: 310 (100) (M$^+$).
IR(KBr) $\upsilon_{max}$: 3360 cm$^{-1}$ (—OH).
$^1$-NMR (DMSO-d$_6$) δ:
  4.46 (2H, d, J=5.3 Hz, —CH$_2$—O—),
  5.27 (1H, t, J=5.3 Hz, —OH),
  5.55 (2H, S,

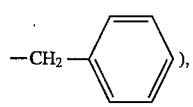), 6.43 (1H, d, J=3.2 Hz, C$_4$-H),
  6.64 (1H, d, J=3.2 Hz, C$_{3"}$-H),
  7.20 (1H, d, J=4.8 Hz, C$_6$-H),
  7.27–7.35 (5H, m, phenyl-H),
  7.72 (1H, d. J=4.8 Hz, C$_5$-H).
Anal. Calcd for C$_{17}$H$_{14}$N$_2$O$_2$S : C, 65.79; H, 4.55; N, 9.03;
Found: C, 65.58; H, 4.70; N, 9.31.

Example I-3-12

1-Benzyl-3-(p-hydroxymethylphenyl)indazole (XI-6)

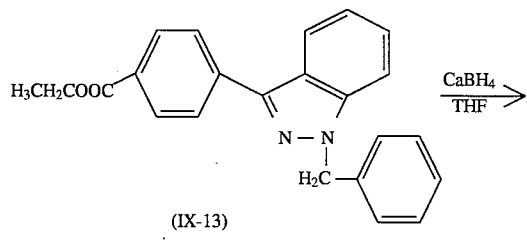

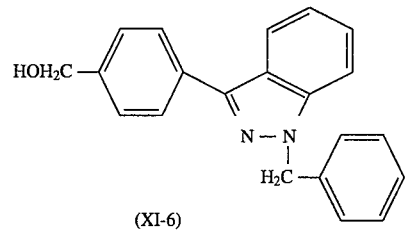

1-Benzyl-3-(p-ethoxycarbonyphenyl)indazole (1X-13) (9.6 g. 0.027 mole) was as the starting material and treated according to the procedure described in example I-3-6 to give compound X1-6, Yiejld 6.4 g (81%)
mp: 110°~112° C.,
MS(%), m/z: 314(100) (M$^+$)
IR(KBr) $\upsilon_{wax}$: 3300–2500 cm$^{-1}$(OH).
$^1$H-NMR (DMSO-d$_6$) δ:
  4.58 (2H, d. J=5.2 Hz, —CH$_2$O—),
  5.31 (1H, t, J=5.2 Hz, OH),
  5.73 (2H, S,

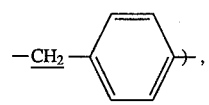, 7.23~8.17 (13H, m, aromatic protons).
Anal. Calcd for C$_{21}$H$_{18}$N$_2$O : C, 80.23; H, 5.77; N, 8.91;
Found: C, 80.45; H, 5.62; N, 8.99.

EXAMPLE 37

A typical tablet which may be prepared by conventional tabletting techniques contains

| | |
|---|---|
| active compound | 40 mg |
| lactose | 30 mg |
| starch | 8 mg |
| mag. stearate | 10 mg |
| corn starch | 12 mg |

(II) Inhibiting Activity on Platelet Aggregation
A. Preparation of Aggregation Inducing Agent
  1. Collagen (bovine tendon) in 15 mM aqueous acetic acid was grounded at 4° C. to form a well dispersed suspension, and dispensed in 1 mg/ml and stocked at −70° C. Before using, it was thawed and well grounded.
  2. PAF was dissolved in CCl$_4$ and stocked at 20° C. Before using, it was diluted with deionized water.
  3. Adenosine(ADP) and sodium arachidonate (AA) were dissolved in deionized water for use.
B. Preparation of Platelets
  A suspension of platelets was prepared according to the reported method. 100 m of EDTA and the blood from rabbit's ear was mixed in the ratio of 1:1, and immediately separated by centrifuge (120 × g) at room temperature for 10 minutes. The platelets enriched upper layer plasma was subjected to centrifuge (500 × g) for 10 minutes. After the plasma was removed, the platelets in lower layer were suspended in the Tyrode solution containing EDTA (2 mM) and bovine serum protein(3.5 mg/ml), and subjected to centrifuge (500 × g) again for 10 minutes. The platelets obtained was suspended in a Tyrode solution containing no EDTA, and was adjusted to about 4.5×10 cell/ml by a counters. 1 m of calcium ion(Ca$^{2+}$) was added to the the suspension. 30 minutes after the addition, the experiment was conducted. The composition, of Tyrode: bovine serum protein, NaCl (136.9), KCl(2.7), Na$_3$PO$_3$(40.4), NaHCO$_3$ (11.9), glucose (11.1).

C. Platelet Aggregation and ATP Release Reaction Test

The method reported by Born,G.V.R.(J.Physiol. 168, 178, 1963) was used to determine the platelet aggregation, in which a Lumi-aggregometer(Model 1020, Payton, Canada) was used. Platelet suspension(0.4 ml) was added into a small glass tube coated with silicone, and stirred at 900 rpm with a small magnetic stirrer. Unless otherwise specified, the antagonist was added 1 minute before the inducing agent, and all the reactions were carried out at 37° C. The aggregation was calculated by following formula:

aggregation(%)=(light absorption before adding inducing agent − light absorption after adding inducing agent) / (light absorption before adding inducing agent − light absorption of Tyrode solution) × 100%

In some experiments, the compounds of formula (A) at the concentration of 100 μg/ml are found to inhibit perfectly the platelet aggregation which was induces by arachidonic acid(AA), ADP, collagen, and PAF. Since the structures of the invention compounds are different from prior anticoagulants, the present invention have a potential for further development.

TABLE 1

Effects of Compound XI-1-5 on the platelet aggregation induced by Arachidonic acid (AA), ADP, Collagen and PAF

| Compounds | concentration (μg/ml) | ADP | AA | Collagen | PAF |
| --- | --- | --- | --- | --- | --- |
| CONTROL |  | 68.5 ± 3.1 | 89.8 ± 0.7 | 79.9 ± 0.7 | 87.9 ± 2.6 |
| XI-1 | 100 | 1.4 ± 1.2*** | 0*** | 4.7 ± 3.0*** | 0*** |
| XI-2 | 100 | 0** | 4.2 ± 3.4*** | 0*** | 0*** |
| XI-3 | 100 | 0*** | 0*** | 0*** | 0*** |
| XI-4 | 100 | 2.8 ± 2.3*** | 18.9 ± 13.3*** | 4.5 ± 3.9*** | 7.7 ± 6.3*** |
| XI-5 | 100 | 1.3 ± 1.1*** | 0*** | 4.7 ± 3.0*** | 0*** |

Washed rabbit platelet was incubated with each compound or 0.5% DMSO (control) at 37° C. for 3 min., then ADP (20 μM), AA (100 μM), Collagen (10 μg/ml) or PAF (2 ng/ml) was added to trigger the aggregation. Percentages of aggregation are presented at mean ± S.E.M. (n = 4), *p < 0.005 p < 0.01 *p < 0.001 as compared with the respective control value.

What claim is:

1. A process for preparing 1-substituted benzyl-3-substitute-aryl condensed pyrazoles, which are represented as compound X below,

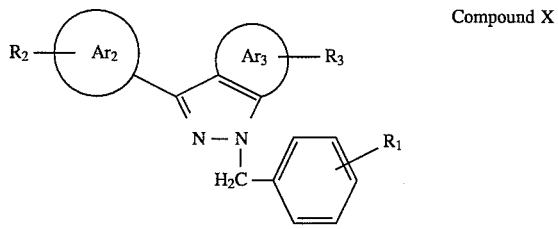

Compound X wherein Ar$_2$ is

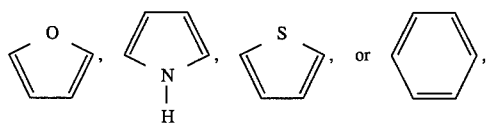

-continued

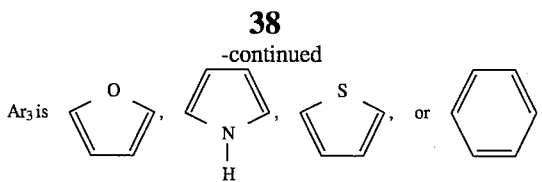

$R_1$ is H, $C_{1-3}$ alkyl, or X where X is a halogen; $R_2$ is CH$_2$OR, H, COOR, $C_{1-3}$ alkyl, or X; $R_3$ is H, $C_{1-3}$ alkyl, X, or —OR radical, and R is H or $C_{1-3}$ alkyl; said process comprising the following steps (a) reacting compound I and compound II, or compound III and compound IV, to produce compound V, which is a substituted aryl ketone, as follows:

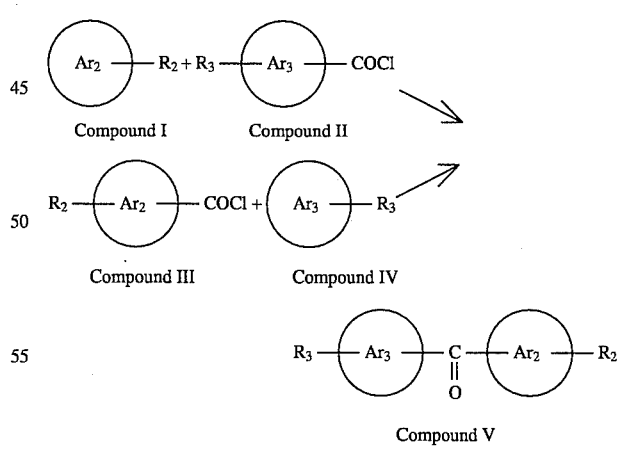

(b) reacting said compound V with a hydrazine compound VI, which is represented by the following formula:

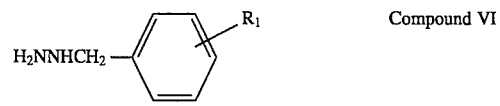

Compound VI to form a hydrazone compound VII, which is represented by the following formula:

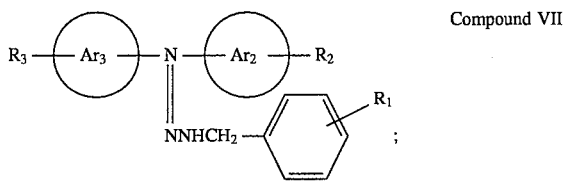

Compound VII (c) reacting said hydrazone compound VII with lead tertraacetate (LTA) to form an intermediate compound VIII, which is represented by the following formula:

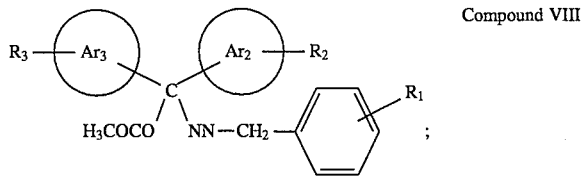

Compound VIII and (d) reacting said intermediate compound VIII with trifluoride etherate ($BF_3.Et_2O$) to form said 1-substituted benzyl-3-substituted-aryl condensed pyrazole.

2. A process for preparing 1-substituted benzyl-3-substituted-aryl condensed pyrazoles according to claim 1 wherein $R_2$ is a —COOR group.

3. A process for preparing 1-substituted benzyl-3-substituted-aryl condensed pyrazoles according to claim 1 wherein $R_3$ is an —OR group.

4. A process for preparing 1-substituted benzyl-3-substituted-aryl) condensed pyrazoles according to claim 1 wherein $R_2$ is a —$COOCH_3$ group, and said process further comprises the step of reacting said 1-substituted benzyl-3-substituted-aryl condensed pyrazole with an acid or a base to form a 1-substituted benzyl-3-hydroxycarbonyl-aryl condensed pyrazole represented by the following formula:

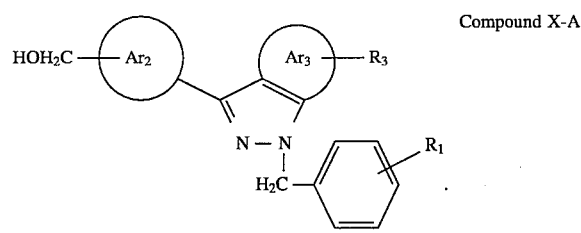

Compound X-A

5. A process for preparing 1-substituted benzyl-3-substituted-aryl) condensed pyrazoles according to claim 1 wherein $R_2$ is a —$COOCH_3$ group, and said process further comprises the step of reacting said 1-substituted benzyl-3-substituted-aryl condensed pyrazole with a strong reducing agent to form a 1-substituted-benzyl-3-hydroxymethyl-aryl condensed pyrazole represented by the following formula:

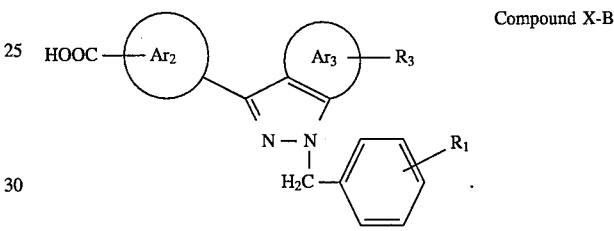

Compound X-B

* * * * *